United States Patent [19]
Eichenlaub

[11] Patent Number: 5,237,873
[45] Date of Patent: Aug. 24, 1993

[54] METHOD OF DETERMINING TYPE OF REFRIGERANT

[76] Inventor: Dennis Eichenlaub, 19 Vista View Court, Kingsville, Md. 21087

[21] Appl. No.: 761,379

[22] Filed: Sep. 18, 1991

[51] Int. Cl.$^5$ .................... G01N 29/18; G01N 25/00
[52] U.S. Cl. .................... 73/597; 73/61.46; 73/61.76; 374/45; 62/127
[58] Field of Search .................... 374/43, 45, 1; 73/25.01, 61.46, 61.76, 597, 1 R, 1 DV, 24.1; 62/127

[56] References Cited

U.S. PATENT DOCUMENTS

| | | | |
|---|---|---|---|
| 1,495,314 | 5/1924 | Walker | 374/45 X |
| 3,093,791 | 6/1963 | Richards | 374/45 X |
| 3,232,069 | 2/1966 | Hawkins | 374/45 X |
| 3,522,580 | 8/1970 | Lynch et al. | 73/597 X |
| 3,538,750 | 11/1970 | Lynnworth | 73/597 X |
| 3,544,276 | 12/1970 | Morwitz, Jr. | 62/125 X |
| 3,648,513 | 3/1972 | Patterson | 73/64.53 |
| 4,479,727 | 10/1984 | Domingorena et al. | 374/45 |
| 4,768,347 | 9/1988 | Manz et al. | 62/149 |
| 4,805,416 | 2/1989 | Manz et al. | 62/292 |
| 4,879,546 | 11/1989 | Dunham et al. | 73/31.02 X |
| 4,923,806 | 5/1990 | Klodowski | 62/127 X |
| 4,939,905 | 7/1990 | Manz | 62/77 |
| 5,158,747 | 10/1992 | Manz et al. | 73/25.04 X |

FOREIGN PATENT DOCUMENTS 1341852 9/1987 U.S.S.R. ................ 73/597

OTHER PUBLICATIONS

"Chamber for High-Pressure Ultrasonic Investigations of Liquids" Instrum. & Exp. Tech. (U.S.A.) vol. 23, No. 6, pp. 1529-1530 Published Jun. 1981, Sh. Kh. Ikramov et al., in 73/597.

Primary Examiner—Tom Noland
Attorney, Agent, or Firm—Cushman, Darby & Cushman

[57] ABSTRACT

A method of identifying refrigerants is disclosed based on an apparatus that first evaporates a refrigerants sample such that all non-condensible contaminants are removed, condenses the refrigerant to a liquid state, then measures the sonic velocity at two different temperatures. Two measurements, taken together, establish the sonic velocity in a temperature coefficient of the sonic velocity, which are used to identify the refrigerant. A self calibration method makes measurements more accurate.

10 Claims, 4 Drawing Sheets

METHOD OF DETERMINING TYPE OF REFRIGERANT

BACKGROUND OF THE INVENTION

1. Field of the invention

This invention relates to systems for identifying refrigerants. More particularly, this invention relates to systems for measuring sonic velocities and temperature coefficients of the sonic velocities as indicia of the type of refrigerant in or from an air conditioning system.

2. Description of the Related Art

Identification of the refrigerant in an air conditioning system will soon become important to the refrigeration industry because refrigerants must be reclaimed and reused, and because new refrigerants are being developed.

Until now, the automotive refrigeration industry used Refrigerant 12 (R12) exclusively in air conditioning systems. However, R12 attacks the atmospheric "Ozone layer", making it particularly damaging to the environment. Therefore, the production of R12 will be gradually discontinued. New refrigerants, such as R134a, are being developed for use in automotive air conditioning systems. However, these refrigerants are not compatible with R12 and require new air conditioning components. Existing automotive air conditioning systems will be serviced using ternary blends. In a few years, the automotive refrigeration industry will be using several different refrigerants. Already, the commercial refrigeration industry uses several different refrigerants.

If an air conditioning system has an unknown refrigerant or a mix of refrigerants and the refrigerant is vented to the atmosphere, the refrigerant in the air conditioner is of no concern. However, if the refrigerant is to be reclaimed, then it is essential to know the type of refrigerant before beginning the reclamation process. This is because once refrigerants are mixed, they cannot easily be separated. A large tank of reclaimed refrigerant is generally ruined if it contains a mixture of different refrigerants. Instead of being reused, a tank containing a mixture of different refrigerants must be incinerated.

In the past, when a refrigeration system needed service, the refrigerant was vented to the atmosphere. Because all refrigerants are greenhouse gases and because some refrigerants attack the atmospheric "Ozone layer", the practice of venting refrigerant to the atmosphere is no longer acceptable. The automotive refrigeration industry already reclaims and reuses refrigerant. The commercial refrigeration industry is now writing standards that will result in reclaiming and reusing refrigerant.

SUMMARY OF THE INVENTION

The present invention provides methods of identifying which refrigerant is in an air conditioner before the refrigerant is reclaimed. If the refrigerant is supposed to be a blend (such as any of the ternary blends that will be used in the automotive market), the present invention can identify whether the blend contains the correct mixture of refrigerants thus making it reusable or whether it contains an incorrect mixture of refrigerants (thus making it unreusable). If the air conditioner contains a mixture of two or more different refrigerants, the gases will be identified as an unusable mixture of refrigerants.

In accordance with the methods of the present invention, the sonic velocity of the refrigerant and the temperature coefficient of the sonic velocity are measured to identify the type of refrigerant in a particular air conditioning system.

BRIEF DESCRIPTION OF THE DRAWINGS

In accordance with these and other objects which will become apparent, the present invention is described below with particular reference to the accompanying drawings, in which.

DETAILED DESCRIPTION OF THE PRESENTLY PREFERRED EMBODIMENTS

GENERAL DESCRIPTION

Figure 1A:
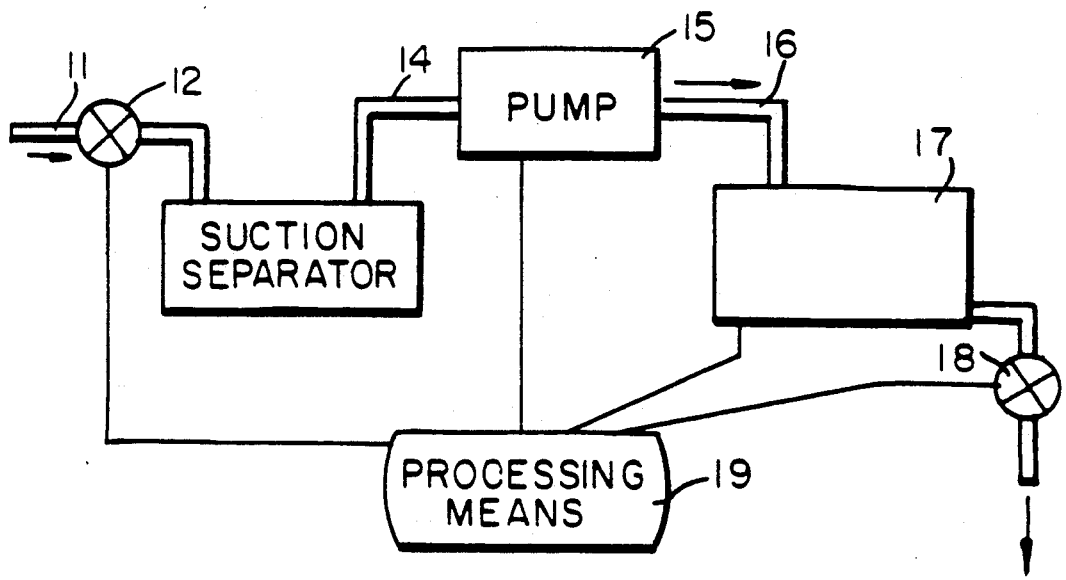
FIGS. 1A and 1B are system diagrams of the present invention according to two embodiments.
Figure 1B:
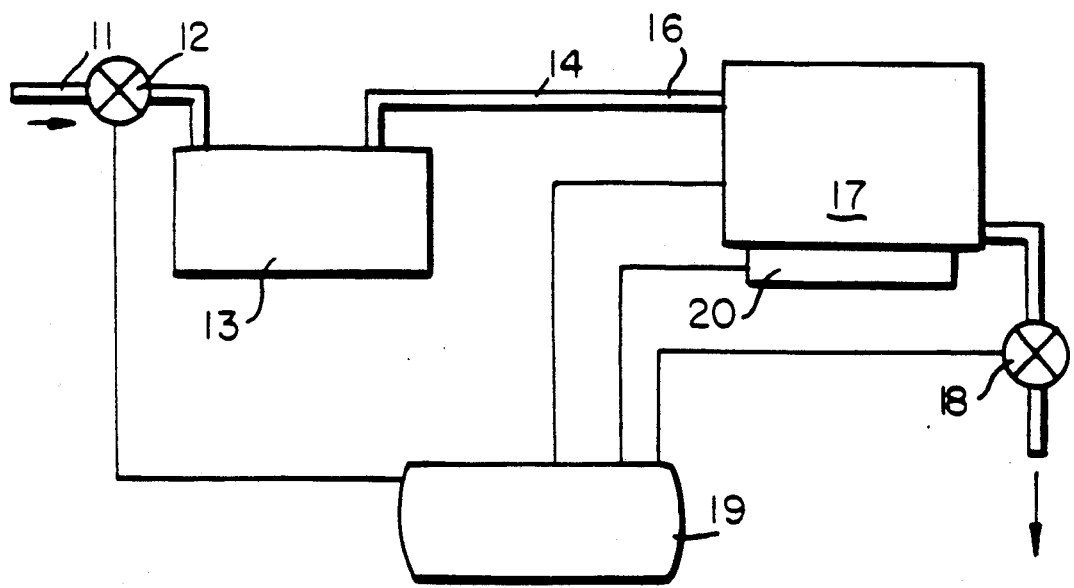

FIG. 1 shows two implementations of the disclosed invention. The implementation in FIG. 1A includes an inlet hose 11, an inlet valve 12, a suction separator 13, a suction separator exhaust pipe 14, a pump 15, a sample inlet 16, a sample chamber assembly 17, an exhaust valve 18, and a processing means 19. FIG. 1B accomplishes the same purpose as FIG. 1A by replacing the pump 15 with a cooling device 20. As will be discussed below, the purpose of this device is to place a volume of liquid refrigerant in the sample chamber assembly without allowing any lubricant or particulate in the sample.

Figure 2A:
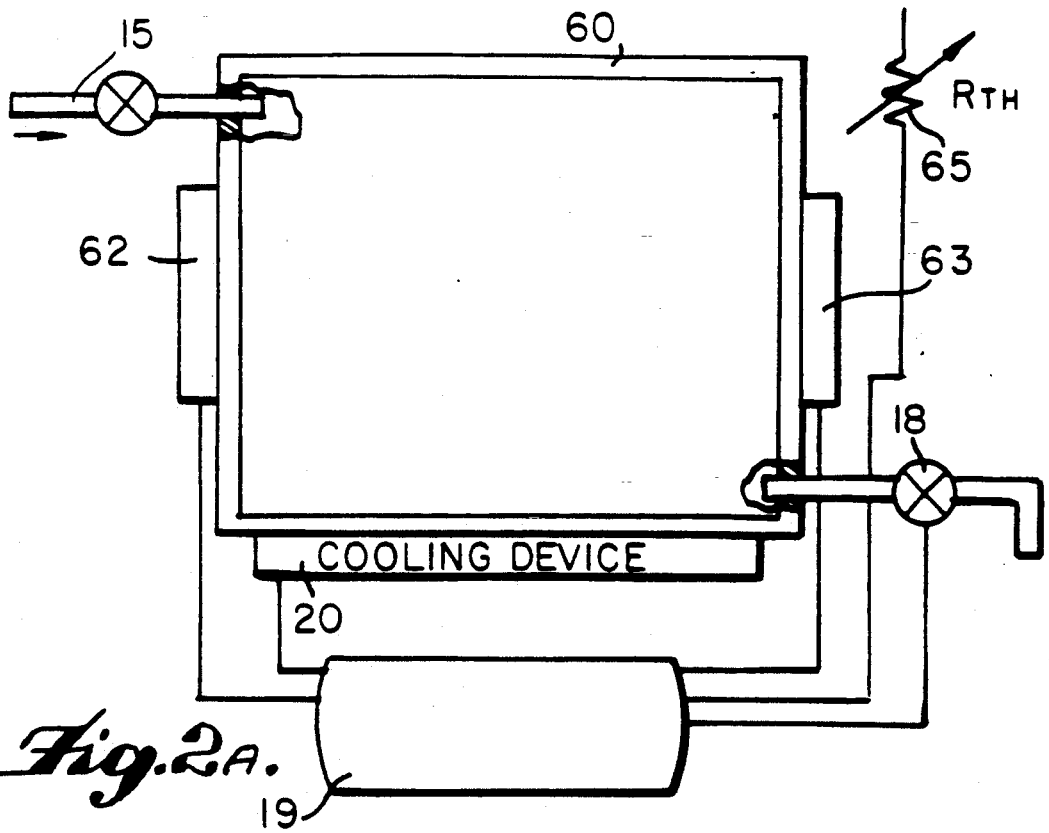
FIGS. 2A and 2B show alternative sample chambers from FIGS. 1A and 1B.
Figure 2B:
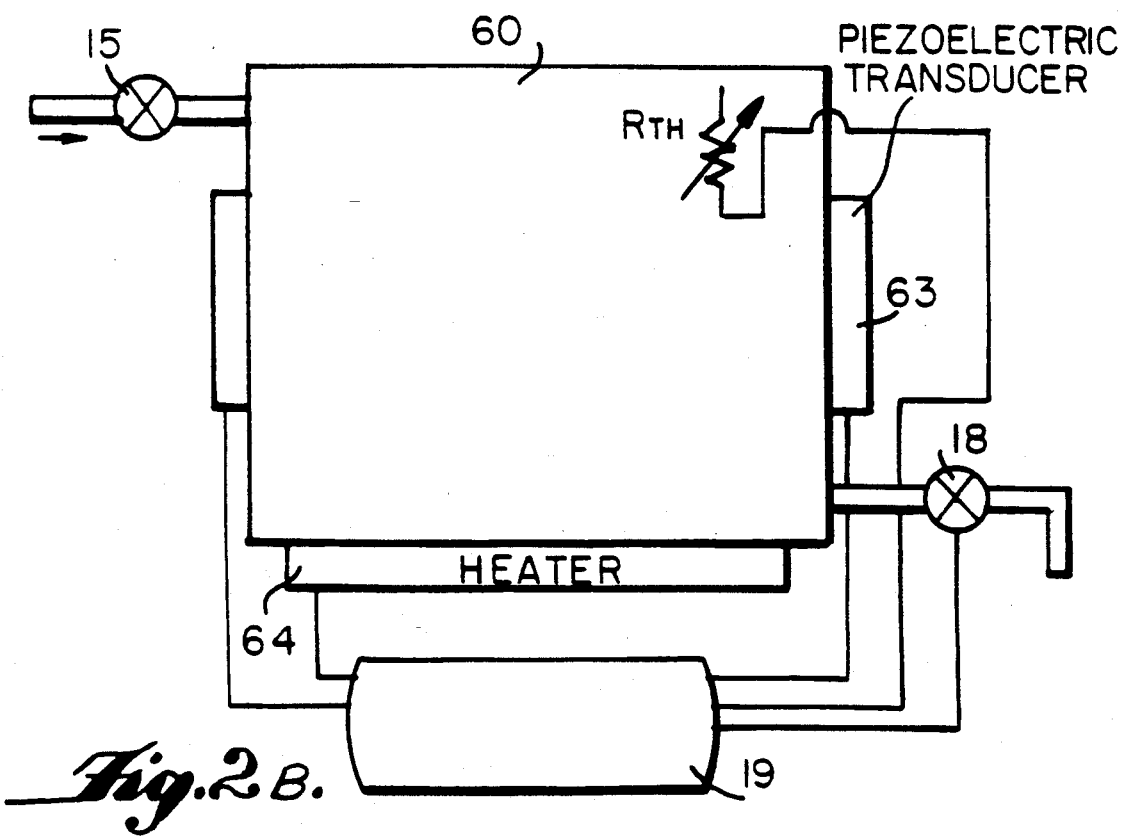

FIGS. 2A and B show possible implementations of the sample chamber in detail. The implementations include the sample chamber 60 which may contain two piezoelectric transducers 62 and 63, the sample inlet 15, the exhaust valve 18, a heater 64 (FIG. 2B) or a cooling device 20 (FIG. 2A), a temperature measurement device 65, and the processing means 19. An alternate implementation does not use the second piezoelectric transducer 63. The purpose of the sample chamber assembly is to measure the sonic velocity and the temperature coefficient of the sonic velocity of the liquid refrigerant in the chamber. These two measurements will allow a determination of which refrigerant is present, as will be discussed below.

IDENTIFYING THE REFRIGERANT

Figure 3:
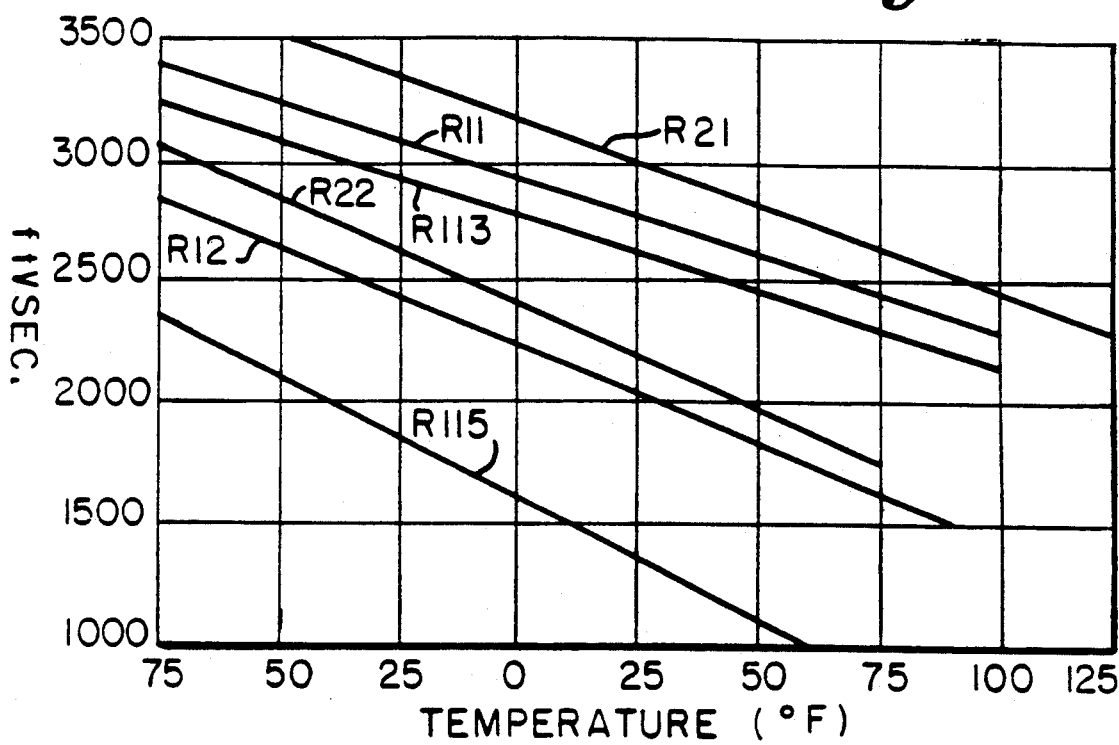
FIG. 3 shows the relationship between sonic velocity and temperature for several refrigerants.

FIG. 3 shows a plot of sonic velocity -vs- temperature for several common refrigerants. Note that these refrigerants have:

1. different sonic velocities at any given temperature,
2. different temperature coefficients for sonic velocity, and
3. temperature coefficients that are constant over a broad temperature range.

With the refrigerants shown in FIG. 3, measuring sonic velocity at any one temperature will uniquely identify a refrigerant. However, three potentially complicating factors must be taken into account to make a refrigeration identification device practical. First, a new refrigerant, not currently in use, might have sonic velocities that are the same as an existing refrigerant at certain temperatures. Second, a mixture of two or more refrigerants might have the same sonic velocity as a third refrigerant at some temperatures. Third, ternary blends are likely to be used and must be identified.

Figure 4:
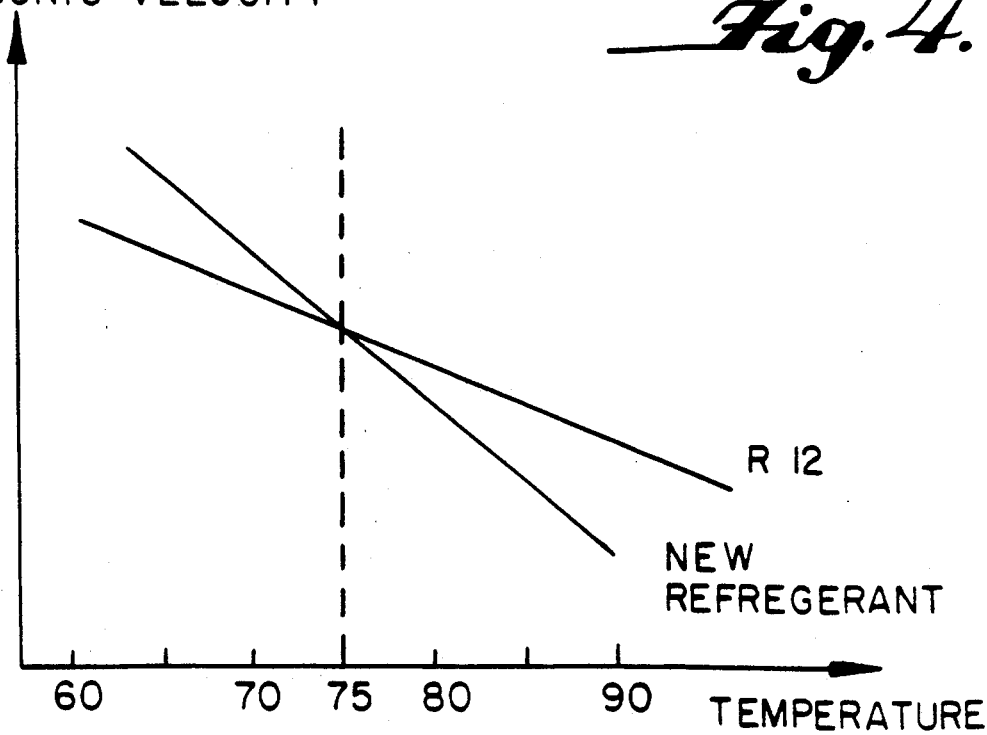
FIG. 4 shows the relationship between sonic velocity and temperature for a known and a hypothetical refrigerant.

FIG. 4 shows the situation where a hypothetical new refrigerant has the same sonic velocity as R12 at 75 degrees. Under this hypothetical example, if the sonic velocity of this refrigerant is measured only at 75 degrees, it would be impossible to determine whether the new refrigerant or R12 is present. However, if the measurement is taken at two different temperatures so that both the sonic velocity and its temperature coefficient are measured (for example, at 75 degrees and 100 degrees), the two refrigerants are easily separated.

Figure 5:
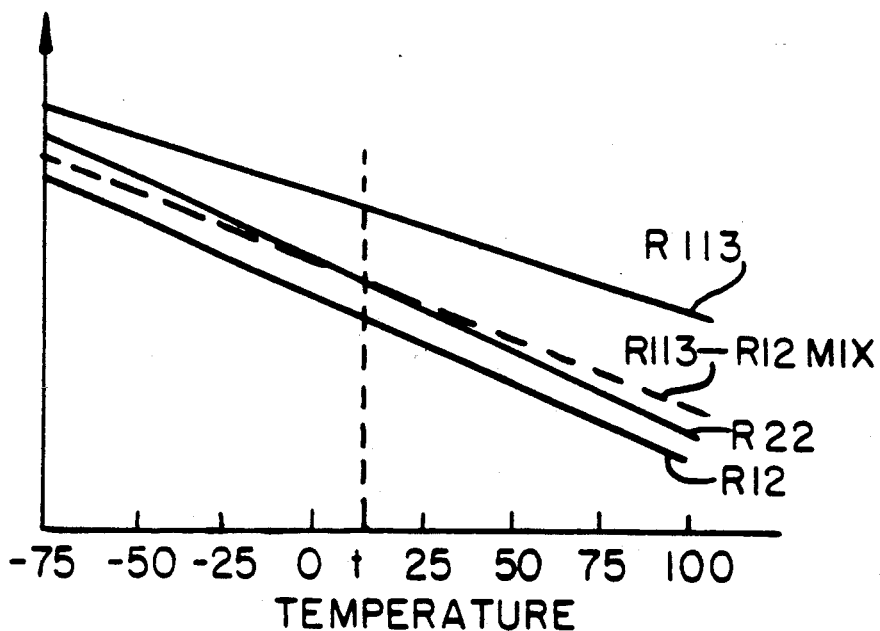
FIG. 5 shows the relationship between sonic velocity and temperature for known refrigerants and a mixture of refrigerants.

A practical refrigerant identification device must be able to identify any mix of refrigerants as unusable. FIG. 5 illustrates the sonic velocity -vs- temperature curve of R12, R22, and R113. If an air conditioner has a mixture of R12 and R113, the mixture will have a sonic velocity -vs- temperature curve that is a composite of the two refrigerants, as shown by the dashed line in FIG. 5. It is possible for such a mixture to have the same sonic velocity as R22 at a given temperature, $t_1$. However, the temperature coefficients of the sonic velocity will also be a composite of the R12 and R113. Since the temperature coefficient of the sonic velocity for the mixture is different than the temperature coefficient of the sonic velocity for R22, measuring the sonic velocity at two temperatures permits the system to correctly differentiate between a usable refrigerant and an unusable mixture of two different refrigerants.

Finally, ternary blends of refrigerants are likely to be used and should be identifiable. Since a ternary blend is a mixture of three different refrigerants, the blend will exhibit a composite sonic velocity and temperature coefficient that is unique, making the blend identifiable as a refrigerant. If differential leakage has significantly changed the composition of the ternary blend, the composite sonic velocity and temperature coefficient will be significantly different, and the refrigerant can be identified as an unusable mix.

COLLECTING THE SAMPLE

If a sample of refrigerant is to be drawn from an air conditioner, the lubricant and any particulate must first be separated from the refrigerant. The procedure for doing this is well known and is widely used in refrigerant reclaim machinery. A hose with a suitable fitting 11 is connected to the air conditioner. An inlet valve 12 is opened to allow refrigerant, lubricant, etc. to flow into a suction separator 13. A suction separator exhaust pipe 14 is arranged so that only gases can leave the suction separator. Since refrigerant will evaporate at normal ambient temperatures but lubricants and particulate will not, only refrigerant leaves the suction separator.

The refrigerant identification device can measure the sonic velocity and temperature coefficient of either gaseous or liquid refrigerant. However, if gaseous refrigerant is to be measured, the sonic velocity will also be a function of gas pressure. Also, air might be a large portion of the sample, leading to invalid measurements. Converting the sample to liquid removes the need to know the pressure of the sample and limits the maximum amount of air to the very small amount of air that can be dissolved in the liquid refrigerant. Converting the refrigerant to the liquid state can be accomplished by placing the sample under pressure with a pump 15 or by cooling the sample until it condenses with a cooling device 20, such as a thermal-electric element or a conventional refrigeration system. Once the measurement is taken, refrigerant is evacuated through the exhaust valve 18. The sequence of accepting refrigerant from the air conditioner, taking the measurement, and exhausting the sample is coordinated by the processing means 19.

DESCRIPTION OF THE MEASUREMENT

Once a suitable sample of refrigerant is collected, the sample is measured to determine which refrigerant is in the sample chamber. The disclosed device makes two measurements to determine the type of refrigerant in the chamber: the sonic velocity and the temperature coefficient of the sonic velocity. It further uses a self calibration process to make accurate measurements practical.

MEASUREMENT OF SONIC VELOCITY

Measuring sonic velocity is a well understood technology. The processing means 19 sends an electrical pulse to the piezoelectric transducer 62, and measures the time required for this pulse to be received by a second piezoelectric transducer 63. Alternatively, the piezoelectric transducer 63 can be omitted if the processor sends an electrical pulse to piezoelectric transducer 62 and measures the time required for this pulse to bounce off the far wall of the sample chamber 60 and return to the piezoelectric transducer 62. The sonic velocity is the time required for the acoustic pulse to travel through the refrigerant divided by the distance the acoustic signal travels.

As is well known, the sonic velocity of a fluid is dependent on temperature. Therefore, the temperature of the sample must be measured with a temperature measurement device 65 such as a thermistor.

MEASUREMENT OF THE TEMPERATURE COEFFICIENT OF THE SONIC VELOCITY

To measure the temperature coefficient of the sonic velocity, the system can:

1. Measure the sonic velocity, $v_1$, and temperature, $t_1$.
2. Change the sample to a second temperature, $t_2$.
3. Measure a new sonic velocity, $v_2$, at temperature $t_2$.
4. Calculate temperature coefficient of the sonic velocity: tempco$=(v_1-v_2)/(t_1-t_2)$.

As long as the temperature coefficient is constant, any two temperatures may be used in these measurements.

SELF CALIBRATION

A refrigerant might have a sonic velocity and a temperature coefficient that are close to a second refrigerant. To permit the system to adequately differentiate between a pure refrigerant and a mix of two or more refrigerants, it is important to make measurements that are as accurate as practical. The accuracy of the measurements are dependent on such factors as the length of the sample chamber, the precision of the chamber's dimensions, the precision of the temperature measurement, the precision of the time delay measurement, and the bandwidth of the piezoelectric transducer(s). It is undesirable to make the length of the sample chamber so long that an excessively large sample is required. The precision of the time delay measurement and the bandwidth of the piezoelectric transducers are parameters that are well understood and easily controlled. However, the precision of the chamber's dimensions and the precision of the temperature measurement can be compensated for with self calibration.

To accomplish self calibration, the sample chamber is filled with a pure refrigerant having known characteristics. The processing means uses the heater 64 or cooling device 20 to vary the temperature of the sample and take sonic velocity readings at each temperature. During calibration, each temperature that might later be used for measuring sonic velocity must be measured. For example, the processing means might measure the sonic velocity at five degree intervals between 40° F. and 120° F. Thereafter, the system must always adjust the sample temperature to be equal to one of these temperatures before measuring the sonic velocity.

Figure 6:
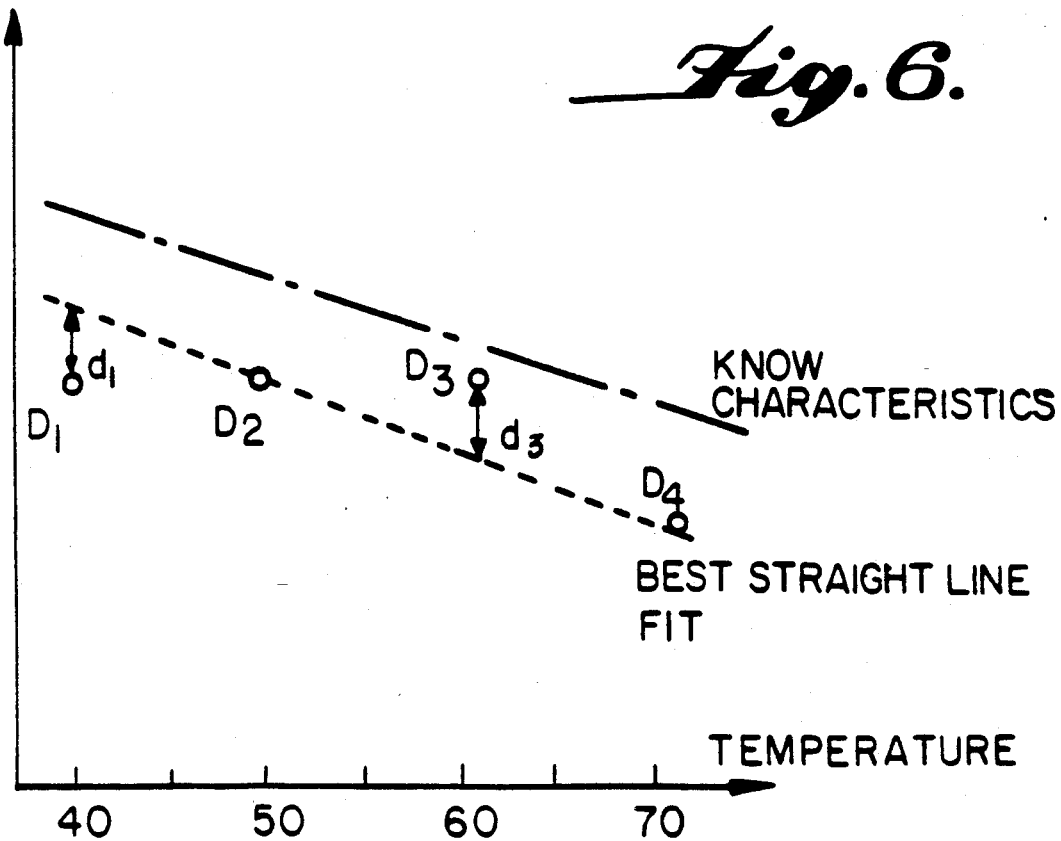
FIG. 6 is a graphic illustration of the self calibration method according to the present invention.

The result of this procedure will be a series of measurements graphically represented as circles on FIG. 6 ($D_1$, $D_2$, $D_3$, etc.). Several calculations must be done to effect the self calibration. First, the best straight line fit of the data points must be found. This is represented by the dashed line in FIG. 6. Next the best straight line fit is compared to the known characteristics of the refrigerant being measured (represented as the dot-dash line in FIG. 6) to determine the error in slope ($e_s$) and offset ($e_b$). The error in slope ($e_s$) and the error in offset ($e_b$) are stored in a suitable memory such as a battery backed RAM or electrically reprogrammable PROM, in the processing means. Finally, the difference between each measurement and the best straight line fit ($d_1$, $d_2$, $d_3$, etc.) is stored separately in a suitable memory in the processing means.

When measuring the sonic velocity of an unknown refrigerant, the processing means must first bring the sample to one of the temperatures used during the calibration process. The sonic velocity measurement, $D_n$, is made. The corresponding difference, $d_n$, is subtracted from the measurement to place the measurement on the best straight line fit. The procedure is repeated at a second temperature. The two measurements form a straight line. This line is corrected by the error in slope, $e_s$, and the error in offset, $e_b$ to form a new straight line. Sonic velocity measurements are calculated based on the new straight line. The corrected numbers are used to ascertain which refrigerant is in the sample chamber.

It is seen that the self calibration system will correct for all systematic errors including errors caused by imprecision in sample chamber dimensions and nonlinearities in the temperature measurement device. The use of self calibration will improve the accuracy of the measurements greatly while at the same time relaxing accuracy requirements on the temperature measurement device and the sample chamber. Further, since self calibration requires only pure refrigerant of known characteristics, it may be done in the field if known good "virgin" refrigerant is used.

While the applicant has described the invention in what the applicant considers the most practical and preferred embodiments, the applicant does not limit the invention to the embodiments described, but intends the invention to cover various modifications and equivalent arrangements within the spirit and scope of the appended claims.

What is claimed is:

1. A system for identifying an unknown refrigerant comprising:
   means for substantially isolating the unknown refrigerant within a housing including:
   an inlet hose and valve;
   a suction separator, connected to the inlet hose and valve; and
   a sample chamber, connected to the suction separator;
   means, operatively connected to the housing, for determining a first sonic velocity of the unknown refrigerant at a first temperature in the housing, for determining a second sonic velocity of the unknown refrigerant at a second temperature in the housing, and for comparing the first sonic velocity at the first temperature and the second sonic velocity at the second temperature to known sonic velocities at the first and second temperatures for known liquid refrigerants.

2. A system for identifying an unknown refrigerant comprising;
   means for substantially isolating the unknown refrigerant within a housing;
   means, operatively connected to the housing, for determining the sonic velocity of the unknown refrigerant at a first temperature in the housing, for determining a temperature coefficient if sonic velocity of the unknown refrigerant, and for comparing the temperature coefficient of sonic velocity at the first temperature to known temperature coefficients of sonic velocity and known sonic velocities at the first temperature for known refrigerants.

3. A system for identifying an unknown refrigerant according to claim 2, wherein:
   the means for determining measures a first sonic velocity of the unknown refrigerant at the first temperature in the housing and measures a second sonic velocity of the unknown refrigerant at a second temperature in the housing, and compares the temperature coefficient of sonic velocity and at least one of the first sonic velocity at the first temperature and the second sonic velocity at the second temperature to known temperature coefficients of sonic velocity and known sonic velocities at the first and second temperatures for known refrigerants.

4. A system for identifying an unknown refrigerant according to claim 2, wherein the refrigerant is a liquid.

5. A system for identifying an unknown refrigerant according to claim 2, wherein the refrigerant is a gas at normal ambient temperature, but the refrigerant is a liquid when the determining means determines the sonic velocity.

6. A system for identifying an unknown refrigerant according to claim 2, wherein the unknown refrigerant is a mixture of refrigerants.

7. A system for identifying an unknown refrigerant according to claim 2, wherein the determining means calibrates the determining of the sonic velocity and the temperature coefficient.

8. A system for identifying an unknown refrigerant according to claim 2, wherein the means for isolating the unknown refrigerant within a housing includes:
   an inlet hose and valve;

a suction separator, connected to the inlet hose and valve; and a sample chamber, connected to the suction separator.

9. A method of identifying an unknown refrigerant, comprising the steps of:
substantially isolating the unknown refrigerant within a housing;
holding the unknown refrigerant at a first temperature while measuring a first sonic velocity of the unknown refrigerant;
determining a temperature coefficient of sonic velocity of the unknown refrigerant;
comparing the first sonic velocity of the unknown refrigerant at the first temperature to a known sonic velocity of a known refrigerant at the first temperature; and
comparing the temperature coefficient of sonic velocity of the unknown refrigerant to a temperature coefficient of a known refrigerant.

10. A method according to claim 9, wherein the steps of determining a temperature coefficient of sonic velocity includes the steps of measuring a second sonic velocity of the unknown refrigerant at a second temperature and processing the first and second sonic velocities and first and second temperatures according to the equation:

$$\text{temperature coefficient of sonic velocity} = \left| \frac{\text{first sonic velocity} - \text{second sonic velocity}}{\text{first temperature} - \text{second temperature}} \right|.$$

* * * * *